US012594002B2

(12) United States Patent
  Bergmann

(10) Patent No.: US 12,594,002 B2
(45) Date of Patent: Apr. 7, 2026

(54) DEVICE FOR MONITORING THE HEALTH OF A PERSON

(71) Applicant: Oxford University Innovation Limited, Oxford (GB)

(72) Inventor: Jeroen Bergmann, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 938 days.

(21) Appl. No.: 16/632,968

(22) PCT Filed: Jun. 14, 2018

(86) PCT No.: PCT/GB2018/051637
  § 371 (c)(1),
  (2) Date: Jan. 22, 2020

(87) PCT Pub. No.: WO2019/020969
  PCT Pub. Date: Jan. 31, 2019

(65) Prior Publication Data
  US 2020/0155033 A1     May 21, 2020

(30) Foreign Application Priority Data

Jul. 26, 2017   (GB) ...................................... 1712031
  Mar. 28, 2018   (GB) ...................................... 1805035

(51) Int. Cl.
  *A61B 5/08*          (2006.01)
  *A61B 5/00*          (2006.01)
      (Continued)

(52) U.S. Cl.
  CPC .......... *A61B 5/0816* (2013.01); *A61B 5/0826* (2013.01); *A61B 5/091* (2013.01);
      (Continued)

(58) Field of Classification Search
  CPC .................. A61B 5/0816; A61B 5/682; A61B 2562/0204; A61B 2562/0219; A63B 71/085
      (Continued)

(56) References Cited

U.S. PATENT DOCUMENTS

2006/0017558 A1*   1/2006   Albert ...................... G08B 3/10
                                                       340/521
2009/0120446 A1    5/2009   Vaska et al.
      (Continued)

FOREIGN PATENT DOCUMENTS

WO        2012/027648 A2    3/2012
WO        2015/048541 A1    4/2015

OTHER PUBLICATIONS

International Search Report & Written Opinion for WO2019/020969 (PCT/GB2018/051637), dated Aug. 30, 2018, pp. 1-10.
      (Continued)

*Primary Examiner* — Puya Agahi
(74) *Attorney, Agent, or Firm* — Thomas|Horstemeyer, LLP

(57) ABSTRACT

A first aspect of the invention provides a device for monitoring the health of a person, comprising: a frame configured to be worn within the mouth of the person; a microphone, mounted to or within the frame, for measuring sound data; and an accelerometer, mounted to or within the frame, for measuring acceleration data; wherein the sound data is for determining breathing data relating to the person's breathing and the acceleration data is for determining impact data relating to an impact experienced by the person.

3 Claims, 2 Drawing Sheets

(51) Int. Cl.

| | | |
|---|---|---|
| *A61B 5/091* | (2006.01) | |
| *A63B 71/08* | (2006.01) | |

(52) U.S. Cl.

CPC ...... *A61B 5/682* (2013.01); *A61B 2562/0204* (2013.01); *A61B 2562/0219* (2013.01); *A63B 71/085* (2013.01); *A63B 2209/00* (2013.01)

(58) Field of Classification Search

USPC ......................................................... 600/538
See application file for complete search history.

(56) References Cited

U.S. PATENT DOCUMENTS

| | | | | |
|---|---|---|---|---|
| 2009/0149722 | A1 | 6/2009 | Abolfathi et al. | |
| 2009/0220921 | A1 | 9/2009 | Abolfathi et al. | |
| 2012/0071741 | A1* | 3/2012 | Moussavi | A61B 7/003 |
| | | | | 600/340 |
| 2012/0172677 | A1 | 7/2012 | Logan et al. | |
| 2014/0134561 | A1 | 5/2014 | Smith et al. | |
| 2014/0187875 | A1* | 7/2014 | Paris | A61B 5/682 |
| | | | | 600/595 |
| 2014/0350354 | A1 | 11/2014 | Stenzler et al. | |
| 2015/0306486 | A1 | 10/2015 | Logan et al. | |
| 2017/0135629 | A1 | 5/2017 | Kent et al. | |
| 2018/0035952 | A1* | 2/2018 | Fraylick | A61B 5/7275 |
| 2018/0091875 | A1* | 3/2018 | Bryson | G08B 21/0453 |
| 2018/0116863 | A1* | 5/2018 | Shah | A61B 5/02055 |
| 2020/0170574 | A1* | 6/2020 | Radmand | A61B 5/291 |
| 2021/0321939 | A1* | 10/2021 | Kent | A61N 1/0548 |

OTHER PUBLICATIONS

International Preliminary Report on Patentability for WO2019/020969 (PCT/GB2018/051637), dated Jan. 28, 2020, pp. 1-7.
JK Search Report for GB Application No. 1712031.2, dated Jan. 24, 2018, pp. 1-5.

* cited by examiner

DEVICE FOR MONITORING THE HEALTH OF A PERSON

CROSS-REFERENCE TO RELATED APPLICATIONS

This application is the National Stage of International Application No. PCT/GB2018/051637, filed Jun. 14, 2018, which claims the priority to GB 1712031.2, filed Jul. 26, 2017 and GB 1805035.1, filed Mar. 28, 2018, which are entirely incorporated herein by reference.

The present invention relates to a device for monitoring the health of a person. In particular, the present invention relates to an intra oral device for measuring a person's breathing and changes to the person's breathing in response to the person experiencing a physical impact.

Recently there has been increased concern in relation to head injuries sustained as a result of physical impact to participants in activities such as contact sports, e.g. rugby, American football or ice hockey, snow sports, e.g. skiing, and motor sports, e.g. motorcycling. There have been attempts to provide devices which detect and measure an impact. For example, in American football, mouth-guards to be worn by players have been developed which measure the force and direction of an impact experienced by the wearer.

Characterising the force of an impact might predict the likelihood of a resulting traumatic brain injury (TBI). However, it does not provide specific information relating the physiological condition of the wearer. It is widely reported that unexpectedly severe symptoms, including death, can result from relatively minor impacts e.g. due to accumulation of damage. Therefore, even impact forces which are not typically associated with TBI can be dangerous. At present, there is no device that can provide information on this.

There is known to be a link between abnormal breathing patterns and acute brain damage. One example of this is impact brain apnoea, in which breathing is suspended following an impact to the head. However, the presence of abnormal or suspended breathing is often overlooked. Further, present trauma management techniques (e.g. rolling a patient supine and compression-only cardo-pulmonary resuscitation) may compound hypoxia caused by abnormal or suspended breathing and worsen the effects of impact brain apnoea.

It is an aim of the present invention to provide a device that at least partially addresses the above problems.

Accordingly, a first aspect of the invention provides a device for monitoring the health of a person, comprising: a frame configured to be worn within the mouth of the person; a microphone, mounted to or within the frame, for measuring sound data; and an accelerometer, mounted to or within the frame, for measuring acceleration data; wherein the sound data is for determining breathing data relating to the person's breathing and the acceleration data is for determining impact data relating to an impact experienced by the person.

Simultaneously collecting data relating to an impact experienced by the wearer of the device and the wearer's breathing allows the device to provide data relating to how the physiological condition of the person changes in response to experiencing an impact. Therefore, the device can provide important and potentially lifesaving data.

The device may further comprise a processor, mounted to or within the frame, for processing the sound data and the acceleration data.

The processor may be configured to determine breathing data relating to the person's breathing based on the sound data. The breathing data may comprise the breathing rate of a person and/or the breathing volume of the person. The breathing data may be time series data. The processing may comprise wavelet analysis.

The processor may be configured to determine impact data relating to a physical impact experienced by the person based on the acceleration data. The impact data may comprise the amplitude of the acceleration of the person and/or the direction of acceleration of the person. The impact data may be time series data.

The processor may be configured to compare the breathing data and the impact data. For example, the device may compare breathing and impact data to determine a correlation between an impact experienced by the person and a change in the person's breathing. The processor may be configured to determine the occurrence of abnormal breathing or cessation of breathing caused by an impact to the person.

Breathing changes in the time-frequency domain may be used to track the physiological effect after impact. The processor may detect changes in, for example, amplitude, frequency and/or shape of the sound and/or breathing data signal that correspond to changes in the physiological state of the person.

It has been recorded that sleep apnoea leads to fatigability, exhaustion and decreased alertness. Fatigue and exhaustion also occurs after TBI and may be present for days in even mild injuries. Perceived physical exhaustion and recovery rates can be determined by tracking breathing patterns after impact. This creates a device that can determine the acute physiological effect of the impact, but also may track early recovery.

Analysis of the gathered device data can be further adapted based on, for example, demographics (i.e. statistical data relating to a specific population and/or particular groups of people) and comparing to previous collected data. The combination of these different datasets may further assist in determining the health of the person.

The frame of the device may be configured to fit conformally with the teeth of the person. In this way, the device can be held securely in the mouth of the wearer.

The frame may be formed from an energy absorbing material. This allows the device to provide a dual function, namely also providing protection to the wearer's teeth during an impact. For example, the device may a mouth guard e.g. for use in contact sports.

The components mounted within the frame may be embedded within the energy absorbing material of the frame. In this way, the user's teeth and mouth are protected from damage by components of the device. The frame may comprise a communicating channel between the microphone and the environment surrounding the device. This improves the performance of the microphone in collecting sound data.

The device may further comprise a communication device, mounted to or within the frame, for transmitting data. The communication device may transmit the data wirelessly. This allows the data collected by the device to be transferred to another device, for example, a mobile phone, tablet or PC. The data may then be analysed or further analysed by the external device. One or more of the sound data, the acceleration data, the processed sound data and the processed acceleration data may be transmitted by the communication device.

According to a second aspect of the invention, there is provided a system comprising: a first device according to the first aspect of the invention; and a second device, separate from the first device, configured to receive data from the communication device of the first device, the second device comprising a second processor for processing the received data.

The second device may be, for example, a mobile phone, tablet or PC. The second processor may be configured to carry out the same functions as the processor described above in relation to the device of the first aspect of the invention. However, the processing may be performed based on data transmitted from the first device to the further device.

According to a third aspect of the invention, there is provided a method of monitoring the health of a person comprising: having the person wear the device of the previous aspects; processing the sound data measured by the device to determine breathing data relating to the person's breathing; and processing the acceleration data measured by the device to determine impact data relating to a physical impact experienced by the person.

Further features and advantages of the present invention are described below by way of non-limiting example with reference to the accompanying drawings, in which.

Figure 1:
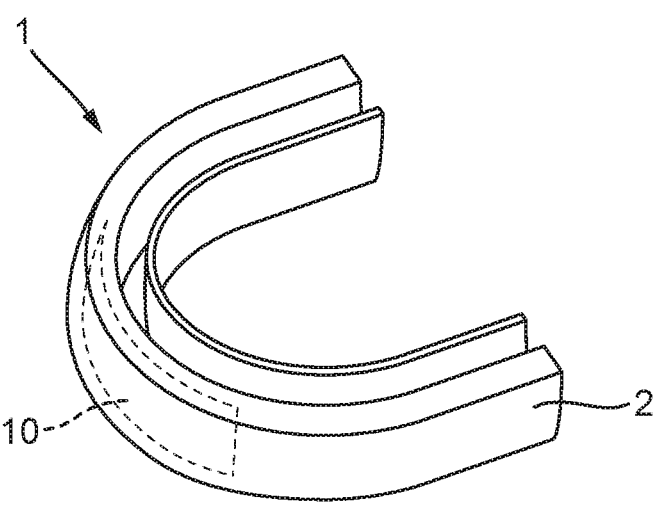
FIG. 1 shows a device according to an embodiment the invention.

FIG. 1 shows an embodiment in accordance with the present invention. As shown, the device 1 comprises a frame 2 and a circuit board 10, e.g. a printed circuit board (PCB). The circuit board 10 comprises the electronic components of the device 1, which will be described in further detail below.

In the embodiment shown in FIG. 1, the device 1 is a mouth guard to be worn by a person, for example when taking part in sports. The frame is formed from an energy absorbing material, e.g. EVA. A PCB 10 is embedded in the material of the frame 2. The frame 2 is formed in a U-shape and also has a U-shaped cross section so as to fit over the teeth of a wearer. The frame 2 may be moulded to fit a specific user. For example, the frame 2 can be manufactured using a mould which is shaped to correspond to the teeth of the wearer. The front section (i.e. corresponding to the location of the wearer's incisors) of the frame 2 may be thicker than the sides to accommodate the PCB 10.

Figure 2:
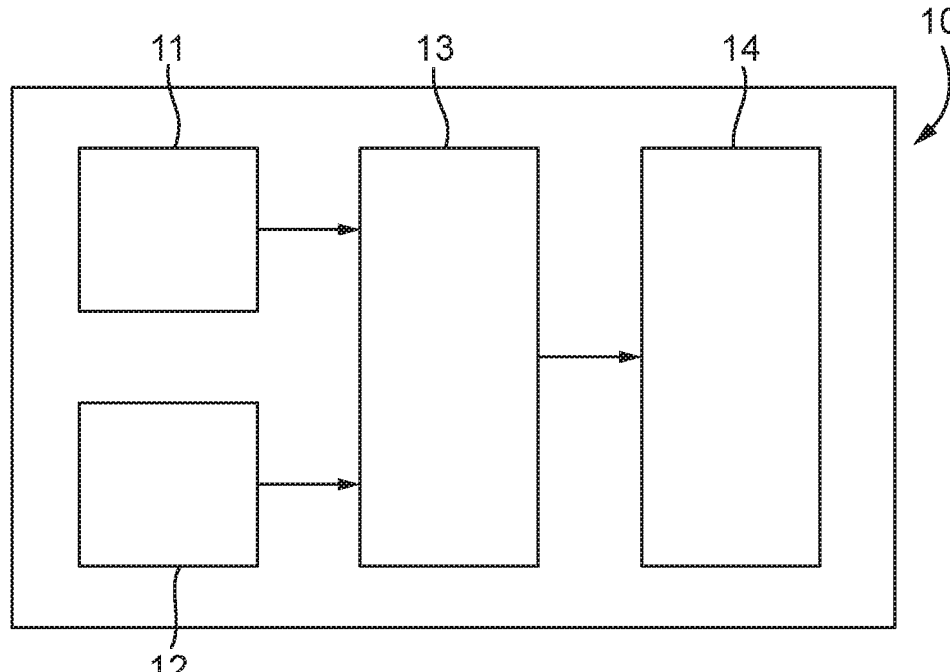
FIG. 2 shows a diagram of electronic components within the device of FIG. 1.

FIG. 2 schematically shows a PCB 10 which comprises a microphone 11, an accelerometer 12, a processor 13 and a communication device 14. Any suitable components may be used. For example, the microphone 11 may be digital MEMS microphone; the accelerometer may be tri-axial MEMS accelerometer; and the communication device may be a low energy Bluetooth microprocessor (e.g., Blue Gecko BGM 12x Bluetooth Smart SIP module). The PCB 10 may also include a battery (not shown) for providing power to the device and means for charging the battery (not shown), e.g. a conductive or inductive wireless charger receiver. The PCB 10 may be flexible or rigid. The PCB may include both flexible and rigid parts. Preferably, the PCB is curved to fit the shape of the frame. However, this is not necessary.

The device shown in FIG. 1 may be manufactured by forming a first layer of the material forming the frame 2, then placing the PCB 10 onto the first layer of the frame 2, then forming a second layer of the material forming the frame 2 over the first layer of material forming the frame 2 and the PCB 10. The two layers forming the frame 2 may formed from the same or different materials.

A communication channel may be provided in the frame 2 between the microphone and the environment surrounding the device. For, example, the channel may be a small hole formed, e.g. drilled, in the frame 2. This allows the microphone to more easily pick up sound from the mouth of the wearer.

The microphone 11 of the device 1 measures sound within the mouth of the wearer of the device 1. The sound within the mouth of the wearer includes sound caused by the wearer's breath during both inhalation and exhalation. However, other sounds may also be picked up by the microphone 11. The data collected by the microphone 11 may be the amplitude of the sound within the mouth of the wearer over a period of time. The microphone 11 may continuously monitor the sound within the mouth of the wearer, e.g. sample the sound at regular intervals at a suitable sampling rate. The sound data may be suitably filtered to extract a signal representative of the breathing of the wearer. In other words, the filters may be used remove noise, e.g. external sound from the external environment of the wearer. The collected sound data may be stored in a memory, e.g. a memory of the processor 13.

Based on the sound data, the processor 13 may determine breathing data relating to the wearer's breathing. The breathing data may include the breathing rate of the wearer. For example, this can be determined based on a wavelet analysis and/or Fourier transform of the sound data and/or another suitable method. Alternatively, or additionally, the breathing data may include the breathing volume (e.g. an estimate of tidal volume) of the wearer, i.e. the volume of air inhaled and/or exhaled by the wearer. This may be determined based on the amplitude of the sound data corresponding to each breath and/or the duration of each breath. The breathing data may be in a form of a time series, which allows changes, e.g. in the breathing rate and breathing volume of the wearer, to be monitored over a period of time. The breathing data may be stored in a memory of the processor 13 for example.

The processor 13 may determine impact data relating to a physical impact experienced by the wearer based on the acceleration data collected by the accelerometer 12. The impact data determined by the processor 13 may include the amplitude of the acceleration and/or the direction of the acceleration. The acceleration data may be filtered to extract useful data. For example, accelerations below a minimum threshold force or in a particular direction may be filtered out, e.g. the low amplitude, regular accelerations caused by movements such as running may be filtered out to provide a useful signal. Therefore, the type of accelerations typically resulting from an impact can be detected more accurately. The impact data may be collected as time series data.

The processor 13 may determine when the wearer's breathing ceases or becomes abnormal. Abnormal breathing may include an abnormally high or low breathing rate, an abnormal, high or low breathing volume, or an irregular breathing rate or breathing volume. The processor 13 may also determine when the wearer stops breathing, i.e. when the wearer's breathing rate is substantially zero.

The processor 13 may compare the breathing data and the impact data to determine whether abnormal breathing or cessation of breathing correlates to a detected impact experienced by the wearer. If the processor 13 determines that abnormal breathing or cessation of breathing may have been caused by an impact experienced by the wearer, one or more actions may be taken automatically. For example, a third party may be notified of the determination, e.g. a team doctor. This may be by wireless communication from the communication device 14. Alternatively, the device 1 may include a light, e.g. an LED, which lights up in response to the processor 13 determining abnormal or cessation of breathing caused by an impact to the wearer.

Figure 3:
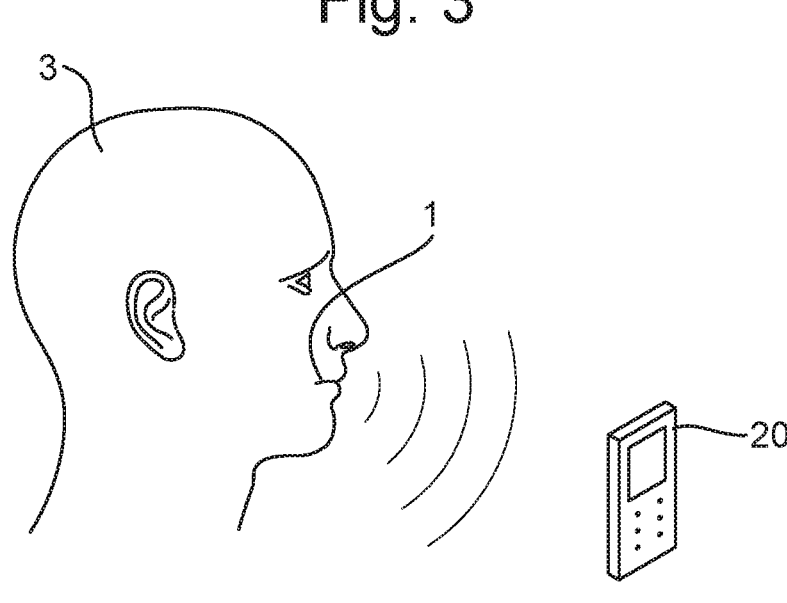
FIG. 3 shows a system according to an embodiment of the invention comprising a first device and a second device.

FIG. 3 shows a second embodiment of the invention. In this embodiment the device shown in FIG. 1 is part of a system comprising the device 1 and an external device 20. The external device 20 may be a mobile phone, tablet or PC for example. The communication device 14 of the device 1 may transmit data to the external device 20. The data transmitted may be the measured sound data or acceleration data or the processed breathing data or impact data.

Figure 4:
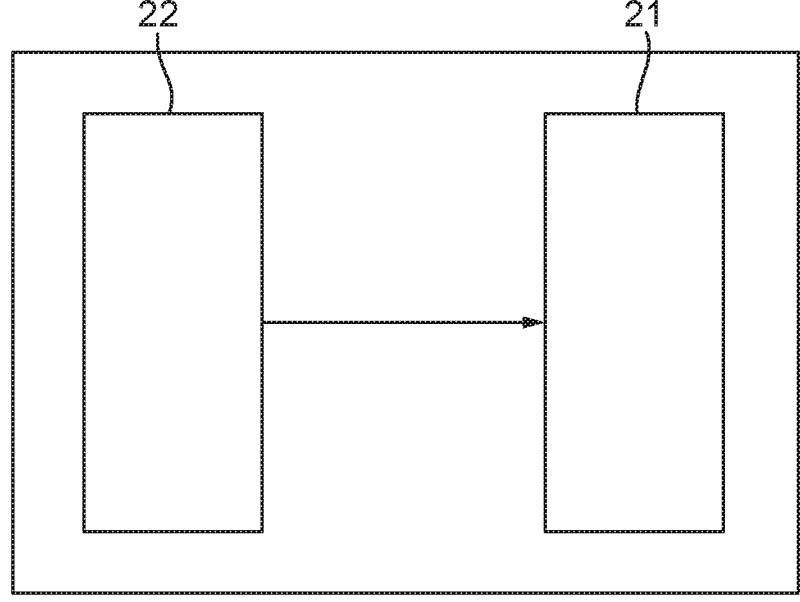
FIG. 4 shows a diagram of the electronic components of the second device of FIG. 3.

The external device 20 may include a processor 21 and a receiver 22 for receiving the data transmitted by the device 1, as shown in FIG. 4. The processor 21 of the external device 20 may perform the same functions as the processor 13 of the device 1 described above. Therefore, the device 1 may not need to perform the processing. This improves the battery life of the device 1 and allows the device 1 to be made smaller.

In an example, data may be transmitted from the device 1 using at least one light source as the communication device 14. The light source may be an LED for example or an array of LEDs. Different LEDs may transmit the different types of data discussed above. Different LEDs may have different colours. The light source may be infrared or near infrared so as to be invisible to the human eye.

The external device 20 may comprise an imaging system (e.g. as a receiver 22) for obtaining image data corresponding to an image of the light source. The processor 21 of the second device 20 may be configured to process the image data to determine the data transmitted by the at least one light source.

The light source 20 may be switched on and off to transmit binary data. The data transmitted by the light source may be any kind of data (e.g. converted into a binary digital signal by the processor 13). Alternatively, the intensity light source may be modulated to provide more continuous, analogue data, as opposed to binary data.

In an example, the light source can be switched on in synchronisation with the inhalation and exhalation of the wearer and switched off in the transition points between inhalations and exhalations. In this way the light source can transmit breathing rate data.

The transmitted data may be detected by an imaging system (e.g. a video or still image camera) of the external device 20. The imaging system may obtain time series image data of the device 1 and the light source. The image data may then be processed by the processor 20 to determine the data transmitted from the device 1 from the image data.

The image processing may comprise a step of detecting a mouth area of the wearer of the device. A facial feature recognition algorithm may be used to determine a region of the image data that corresponds to a mouth of the wearer. The algorithm may be based on a Viola-Jones object detection method. The algorithm may determine a mouth area in a next frame of the image data based on a mouth area determined in a previous frame to improve determination accuracy. The algorithm may determine the mouth area based on the relative location of a number of possible mouth areas. For example, the algorithm may detect the mouth and the eyes as possible mouth regions. Therefore, the correct mouth region can be determined based on which possible mouth region is lowest in the image frame or the distance between the possible mouth regions (the distance between the eyes is usually smaller than the distance from an eye to the mouth). The algorithm may search for the presence of a light source (e.g. based on the colour of the light source) to determine the mouth region.

The image processing may comprise a step of filtering the image data (e.g. the determined mouth area) based on the colour of the light source. The filter may be implemented using a Kaiser Window and/or a Blackman Window, for example. The image processing may further comprise a step of thresholding the image data. For example, pixels below a predetermined threshold may be floored (e.g. assigned a value of zero) and pixels exceeding the threshold may be ceilinged.

The image processing may further comprise a step of determining whether the light source is on or off based on whether the number of non-zero pixels of the thresholded image data exceeds a predetermined threshold. If the number of non-zero pixels exceeds the threshold, then the light source may be determined to be on for that frame.

Processing each frame as above, can provide time-series data (e.g. breathing rate data). This time-series data can be processed further, as described above.

A light source (e.g. an LED of a different colour) may alternatively or additionally be used to transmit acceleration data obtained by the accelerometer. For example, the light source may be switched on (or off) when the wearer experiences an acceleration exceeding a particular threshold, e.g. indicating a forceful impact. The same image processing as described above may be used to determine time-series acceleration data. If different light sources are used for breathing rate data and acceleration data, the breathing rate data and the acceleration data can be compared.

Although the present invention has been described in terms of exemplary embodiments, it is not limited thereto. It should be appreciated that variations or modifications may be made to the embodiments described without departing from the scope of the present invention as defined by the claims.

The invention claimed is:

1. A mouthguard configured to determine an occurrence of impact brain apnoea in a person, automatically, in situ and in real time, caused by an impact suffered by the person while the person is competing in contact sports, snow sports or motor sports, the mouthguard comprising:

a frame configured to be worn within a mouth of the person and surround one or more of the person's teeth, the frame being formed from an energy absorbing material and configured to provide protection to the person's teeth during said impact suffered by the person;

a microphone, embedded within the energy absorbing material of the frame, configured to measure sound data relating to the person's breathing;

an accelerometer, embedded within the energy absorbing material of the frame, configured to measure acceleration data relating to said impact suffered by the person;

a wireless communication device, embedded within the energy absorbing material of the frame, configured to wirelessly transmit data; and at least one processor, embedded within the energy absorbing material of the frame, configured to:

process, automatically and in real time, the sound data measured by the microphone to determine breathing data including a breathing rate of the person and/or a breathing volume of the person, wherein the breathing data is time series data;

process, automatically and in real time, the acceleration data measured by the accelerometer to determine impact data including an amplitude of acceleration of the person during said impact suffered by the person and/or a direction of acceleration of the person during said impact suffered by the person, wherein the impact data is time series data;

compare, automatically and in real time, the breathing data and the impact data to determine a correlation between the breathing data and the impact data;

determine, automatically and in real time, a cessation of breathing caused by said impact suffered by the person, based on the determined correlation between the breathing data and the impact data, thus determining the occurrence of impact brain apnoea suffered by the person; and control the wireless communication device, automatically and in real time, to communicate the determination of the occurrence of impact brain apnoea suffered by the person to an external device.

2. The mouthguard of claim 1, wherein the frame is configured to fit conformally with the person's teeth.

3. The mouthguard of claim 1, wherein the frame comprises a communicating channel between the microphone and an environment surrounding the mouthguard, wherein the channel is a hole formed in the energy absorbing material of the frame configured to allow the microphone to more easily pick up sound from the mouth of the wearer.

\*  \*  \*  \*  \*